(12) United States Patent
Hubelbank

(10) Patent No.: US 12,642,573 B2
(45) Date of Patent: Jun. 2, 2026

(54) ELECTROSURGICAL SYSTEM WITH ELECTRODE ASSEMBLY AND ACCESSORY CHARGE CIRCUIT

(71) Applicant: Medtronic Advanced Energy LLC, Minneapolis, MN (US)

(72) Inventor: David Hubelbank, Minneapolis, MN (US)

(73) Assignee: Medtronic Advanced Energy LLC, Minneapolis, MN (US)

( * ) Notice: Subject to any disclaimer, the term of this patent is extended or adjusted under 35 U.S.C. 154(b) by 0 days.

(21) Appl. No.: 18/400,168

(22) Filed: Dec. 29, 2023

(65) Prior Publication Data

US 2024/0130777 A1 Apr. 25, 2024

Related U.S. Application Data

(62) Division of application No. 16/100,507, filed on Aug. 10, 2018, now Pat. No. 11,871,980.

(60) Provisional application No. 62/543,497, filed on Aug. 10, 2017.

(51) Int. Cl.
*A61B 18/12* (2006.01)
*A61B 18/00* (2006.01)

(52) U.S. Cl.
CPC *A61B 18/1206* (2013.01); *A61B 2018/00023* (2013.01); *A61B 2018/00589* (2013.01); *A61B 2018/00595* (2013.01); *A61B 2018/00607* (2013.01); *A61B 2018/0063* (2013.01); *A61B 2018/1226* (2013.01); *A61B 2018/1253* (2013.01); *A61B 2018/126* (2013.01); *A61B 2018/1266* (2013.01)

(58) Field of Classification Search
CPC ...... A61B 18/1206; A61B 2018/00607; A61B 2018/1253; A61B 2018/126
See application file for complete search history.

(56) References Cited

U.S. PATENT DOCUMENTS

| | | | |
|---|---|---|---|
| 6,113,596 A * | 9/2000 | Hooven | A61B 18/14 606/42 |
| 2008/0287948 A1 * | 11/2008 | Newton | A61B 18/1206 606/50 |
| 2013/0289591 A1 | 10/2013 | Boudreaux et al. | |
| 2015/0190189 A1 * | 7/2015 | Yates | A61B 18/1206 606/34 |
| 2016/0157920 A1 | 6/2016 | Vayser et al. | |

(Continued)

OTHER PUBLICATIONS

Application and file history for U.S. Appl. No. 16/100,507, filed Aug. 10, 2018, inventor Hubelbank, as available in Patent Center.

*Primary Examiner* — Joseph A Stoklosa
*Assistant Examiner* — Annie L Shoulders
(74) *Attorney, Agent, or Firm* — Husch Blackwell LLP

(57) ABSTRACT

An electrosurgical system having an electrosurgical device, an accessory charging circuit, and an electrosurgical unit is disclosed. The electrosurgical device is operable in at least one of a monopolar mode and a bipolar mode. The electrosurgical unit electrically is coupled to the electrosurgical device and the accessory charging circuit. The electrosurgical unit provides one of a monopolar RF energy signal and a bipolar RF energy signal to the electrosurgical device corresponds with an activated mode and a bipolar signal to the accessory charging circuit.

13 Claims, 4 Drawing Sheets

(56)                    References Cited

U.S. PATENT DOCUMENTS

| | | |
|---|---|---|
| 2016/0374752 A1 | 12/2016 | Hancock et al. |
| 2017/0042604 A1 | 2/2017 | McFarland et al. |
| 2017/0090507 A1 | 3/2017 | Wiener et al. |
| 2017/0189096 A1 | 7/2017 | Danziger et al. |
| 2019/0133670 A1 | 5/2019 | Hubelbank |

* cited by examiner

ELECTROSURGICAL SYSTEM WITH ELECTRODE ASSEMBLY AND ACCESSORY CHARGE CIRCUIT

CROSS-REFERENCE TO RELATED APPLICATIONS

This application is a divisional of U.S. application Ser. No. 16/100,507, filed Aug. 10, 2018, which claims the benefit of U.S. Provisional Application No. 62/543,497, filed Aug. 10, 2017, titled "ELECTROSURGICAL SYSTEM WITH ELECTRODE ASSEMBLY AND ACCESSORY CHARGE CIRCUIT," the disclosures of which are hereby incorporated by reference herein.

BACKGROUND

This disclosure relates generally to the field of medical devices, systems and methods for use in surgical procedures. More specifically, this disclosure relates to aspects and features of electrosurgical systems and methods that provide for cutting, coagulation, hemostasis, or sealing of bodily tissues with an electrosurgical device coupled to an electrosurgical unit.

Electrosurgery includes such techniques as cutting, coagulation, hemostasis, or sealing of tissues with the aid of electrodes energized with a suitable power source. Typical electrosurgical devices apply an electrical potential difference or signal between an active electrode and a return electrode on a patient's grounded body in a monopolar arrangement or between an active electrode and a return electrode on the device in bipolar arrangement to deliver electrical energy to the area where tissue is to be affected. The electrosurgical devices are typically held by a clinician, such as surgeon, and connected to the power source, such as an electrosurgical unit having a power generator, via cabling.

Electrosurgical devices pass electrical energy through tissue between the electrodes to provide coagulation to control bleeding and hemostasis to seal tissue. Electrosurgical devices can also cut tissue through the use of plasma formed on the electrode. Tissue that contacts the plasma experiences a rapid vaporization of cellular fluid to produce a cutting effect. Typically, cutting and coagulation are often performed with electrodes in the monopolar arrangement while hemostasis is performed with electrodes in the bipolar arrangement.

Electrical signals can be applied to the electrodes either as a train of high frequency pulses or as a continuous signal typically in the radiofrequency (RF) range to perform the different techniques. The signals can include a variable set of parameters, such as power or voltage level, waveform parameters such as frequency, pulse duration, duty cycle, and other signal parameters that may be particularly apt or preferred for a given technique. For example, the clinician could cut tissue using a first RF signal having a set of parameters to form plasma and control bleeding using a second RF signal having another set of parameters more preferred for coagulation. The clinician could also use electrodes in a bipolar arrangement or a bipolar electrosurgical device for hemostatic sealing of the tissue that would employ additional RF signals having another set of parameters.

In some examples, two distinct electrosurgical devices, one monopolar and the other bipolar, are used to perform different functions in surgery, such as tissue cutting and coagulating and tissue sealing. For example the clinician could use a monopolar electrosurgical device to cut and coagulate tissue and use a bipolar electrosurgical device to seal the tissue. When different techniques or functions were performed during a surgical procedure, the clinician can switch between different devices. Switching between devices can lead to undesirable effects such as longer procedure times, longer response times to issues that unexpectedly develop during surgery, higher costs, and an increased likelihood of inaccuracy or imprecision.

In another example, some electrosurgical devices are capable of performing multiple techniques such as cutting and coagulating tissue or cutting, coagulating, and sealing tissue, including fluid-assisted sealing of tissue. Several such electrosurgical device are described, for example, in U.S. Pat. No. 8,632,533 to Greeley, et al., U.S. Patent Application Publication No. 2012/000465 to Conley, et al., U.S. Patent Application Publication No. 2011/0178515 to Bloom et al., U.S. Patent Application Publication No. 2016/0045250 to Sylvester, et al., U.S. Patent Application Publication No. 2017/0172646 to Patel, et al., U.S. Patent Application Publication No. 2017/0056099 to Hubelbank, et al., each assigned to the assignee of the present disclosure and incorporated by reference herein in their entireties to the extent they are not inconsistent with the present disclosure. Having multiple functions on a single, multipurpose electrosurgical device eliminates or reduces interruption in changing devices that can reduce surgical time.

In some examples, several such multifunction electrosurgical devices that have been developed include a hand piece having two electrodes that are capable of selectively operating in a monopolar mode and a bipolar mode. These devices can be configured as bipolar electrodes connected to a source of bipolar power to operate in a bipolar mode, for example to seal tissue. To operate the same two-electrode device in a monopolar mode, for example to cut tissue, one of the two electrodes may be selectively deactivated and the other of the two electrodes coupled to a source of monopolar power. In this manner, the multifunction device may provide treatment to tissue utilizing one or both electrodes depending upon the desired tissue treatment.

In other examples, a multifunction surgical device can be configured using a plurality of monopolar electrodes that are separately activated and each operated in a monopolar mode. For example, a first monopolar electrode configured as a monopolar blade can be specifically constructed for cutting or desiccating tissue and operated with cutting and coagulating RF energy, which is performed with a relatively high impedance electrode and a high current density to form plasma. A second monopolar electrode can be specifically configured to perform the techniques of hemostatic tissue sealing, which is performed with a relatively lower impedance electrode and a lower current density and a dispersed fluid. Thus, a clinician can perform multiple electrosurgical functions without having to change devices, or from monopolar to bipolar mode or vice versa.

Electrosurgical devices can be operated with electrosurgical units that can include monopolar and bipolar outputs and detect which activation switch on the device is selected. One such electrosurgical unit is available under the trade designation AEx from Medtronic Advanced Energy of Portsmouth, New Hampshire. The electrosurgical unit, in one example, uses a topology of circuit elements, such as a resistor ladder or other circuit configuration, to determine which activation switch of a connected electrosurgical device is selected. In the example, the electrosurgical unit can provide RF signals corresponding with at least three electrosurgical functions such as hemostatic sealing in bipolar configuration, cutting in monopolar configuration, and coagulation in monopolar configuration.

Some electrosurgical procedures can benefit from supplementary functions in addition to the described electrosurgical functions. Such supplementary functions can include illumination, cooling, heating, fluid control, or other functions that can be provided by accessories such as lights, heating or cooling elements, motors, and other accessories at or near the surgical site. A device with a light emitting diode adapter accessory is described in U.S. Pat. No. 8,506,565 to DeCarlo, which is incorporated by reference herein in its entirety to the extent it is not inconsistent with the present disclosure. In some examples, these accessories can be carried on or controlled with the electrosurgical device. Additionally, the electrosurgical device can carry or control multiple accessories or interchangeable accessories. In many examples, a clinician would prefer to have such supplementary functions incorporated into the electrosurgical device to avoid adverse affects of switching between the electrosurgical device and the accessory similar to switching between a separate monopolar device and bipolar device or to simultaneously apply the electrosurgical function and the supplementary function.

Difficulties exist in providing power to such accessories. For example, many electrosurgical units do not include separate outputs, such as RF outputs and direct current (DC) outputs, to simultaneously or separately power accessories for supplementary functions and the electrodes for electrosurgical functions. Simply using the power provided from the electrosurgical unit for both the electrosurgical function and the supplementary function can inhibit one or both of the functions. For instance, some accessories may draw more power than others, and power configuration for some supplementary functions may interfere with the amount of power used by the electrosurgical functions. Batteries may be inconvenient if they are to be replaced during surgery.

SUMMARY

This summary is provided to introduce a selection of concepts in a simplified form that are further described below in the Detailed Description.

The disclosure relates to an electrosurgical unit to provide power to electrosurgical accessories such as lights, motors, heating or cooling elements, fluid control, or other features that may use power for a direct current.

In one aspect, the disclosure relates to an electrosurgical system having an electrosurgical device, an accessory charging circuit, and an electrosurgical unit. The electrosurgical device is operable in at least one of a monopolar mode and a bipolar mode. The electrosurgical unit electrically is coupled to the electrosurgical device and the accessory charging circuit. The electrosurgical unit provides one of a monopolar RF energy signal and a bipolar RF energy signal to the electrosurgical device corresponds with an activated mode and a bipolar signal to the accessory charging circuit.

In one aspect, the disclosure relates to an electrosurgical unit suitable for coupling to an electrosurgical device and an accessory charging circuit. The electrosurgical unit includes bipolar circuitry to logic circuitry. The bipolar circuitry provides a bipolar energy signal and a bipolar RF energy signal. The logic circuitry is operably coupled to the bipolar circuitry to selectively output one of the bipolar energy signal and a bipolar RF energy signal in response to an activation signal based on whether the electrosurgical device is to be configured in a bipolar mode.

In one aspect, the disclosure relates to a method for operating an electrosurgical system. The method determines whether a bipolar mode or monopolar mode of an electrosurgical device has been activated. A monopolar active circuit and bipolar active and return circuits are coupled in electrical connection with an output connection and activating one of monopolar circuitry and bipolar circuitry based on which of the monopolar mode and the bipolar mode of the electrosurgical device has been activated. The bipolar active circuit is coupled in electrical connection with the output connection and the bipolar circuitry is activated if the electrosurgical device is not activated.

In one aspect, the disclosure relates to an electrosurgical system having an electrosurgical device, an electrosurgical unit, and an accessory charging circuit. The electrosurgical device is operable in at least one of a monopolar mode and a bipolar mode. The electrosurgical unit is electrically coupled to the electrosurgical device. The accessory charging circuit includes a rectification circuit electrically coupled to the electrosurgical unit and an energy storage element electrically coupled to the rectification circuit.

DETAILED DESCRIPTION

Figure 1:
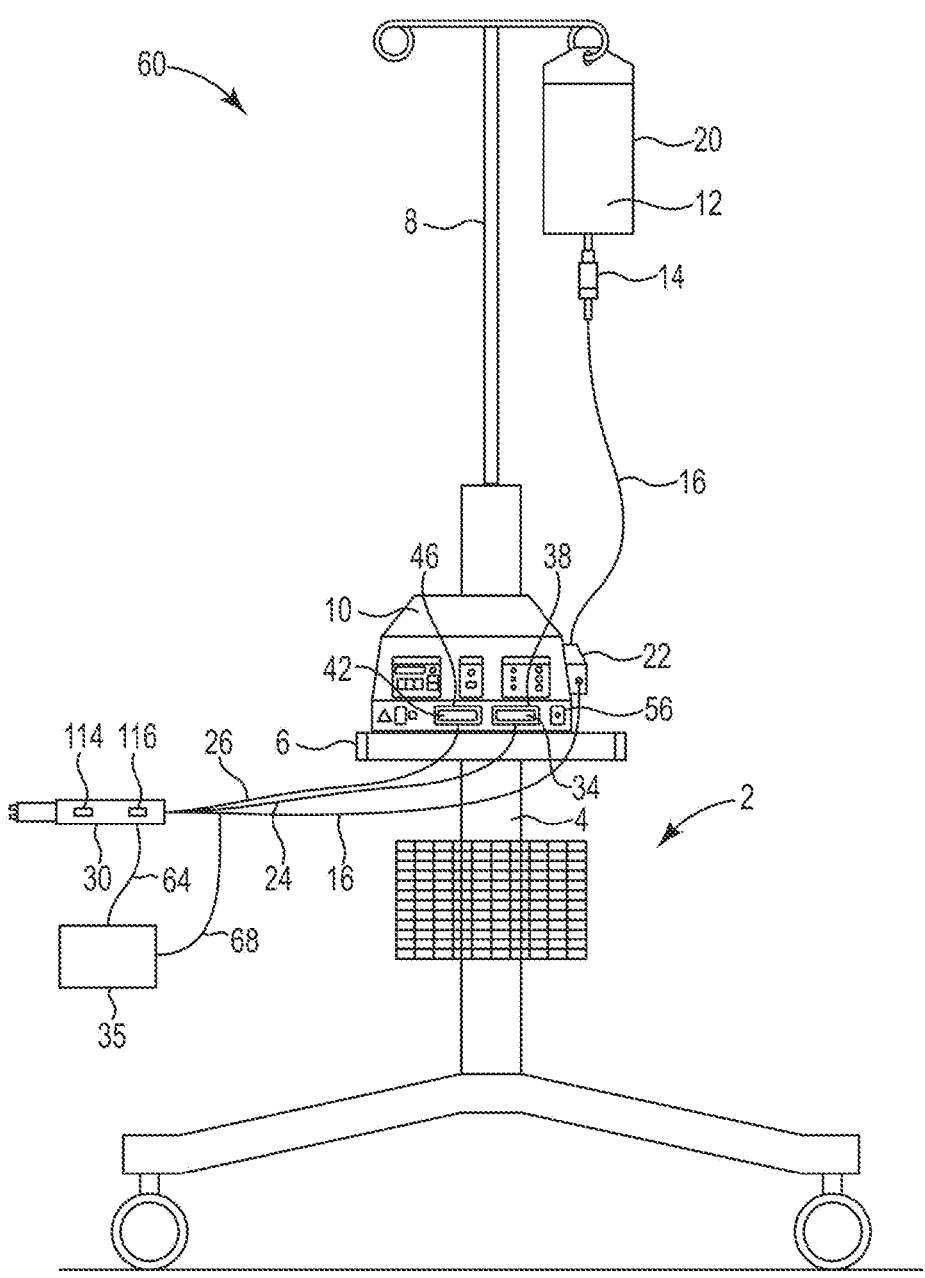
FIG. 1 is a front view illustrating an example of a system according to the present disclosure including an example electrosurgical unit in combination with a fluid source, an example accessory charging circuit, and example handheld electrosurgical device.

Throughout the description, like reference numerals and letters indicate corresponding structure throughout the several views. Also, any particular features(s) of a particular exemplary embodiment may be equally applied to any other exemplary embodiment(s) of this specification as suitable. That is, features between the various exemplary embodiments described herein are interchangeable as suitable and may not be exclusive. From the specification, it should be clear that the terms "distal" and "proximal" are made in reference to a user of the device.

FIG. 1 illustrates a front view of one example of a system 60 that includes an electrosurgical unit 10 in combination with an example handheld electrosurgical device 30 and an accessory charging circuit 35 in which the electrosurgical unit 10 provides RF energy to the device 30 and charging circuit 35. The device 30, in one example, can be a multi-function electrosurgical device configurable for use in cutting and sealing including electrocautery and coagulation in a first mode, such as a monopolar mode or a first monopolar mode, and can be configured to provide for hemostatic sealing of tissue (which may include bone) in combination with a fluid source 20 in a second mode, such as a bipolar mode or a second monopolar mode, or for other electrical surgical procedures. In other examples, the device 30 may be configured to provide limited functions, such as configured for use in cutting and sealing including electrocautery and coagulation such as in a monopolar mode or configured for use in hemostatic sealing of tissue in combination with a fluid source 20 such as in a bipolar mode.

The system 60 can be carried on a movable cart 2 having a support member 4 comprising a hollow cylindrical post which includes a platform 6 comprising a pedestal table to provide a flat, stable surface for location of the electrosurgical unit 10. Cart 2 can include a pole 8 having a height that can be adjusted by sliding the pole 8 up and down. Fluid source 20 can be supported at the top of pole 8.

Fluid source 20 may comprise a bag of fluid from which fluid 12 may flow through a drip chamber 14, to delivery tubing 16 and to handheld electrosurgical device 30. In one example, the fluid 12 includes saline and can include physiologic saline such as sodium chloride (NaCl) 0.9% weight/volume solution. Saline is an electrically conductive fluid, and other suitable electrically conductive fluids can be used. In other examples, the fluid may include a nonconductive fluid, such as deionized water, which may still provide advantages over using no fluid and may support cooling of portions of electrosurgical device 30 and tissue or reducing the occurrence of tissue sticking to the electrosurgical device 30.

The fluid delivery tubing 16 in the example passes through pump 22 to convey fluid to the electrosurgical device 30 and control fluid flow. Pump 22 in one example is a peristaltic pump such as a rotary peristaltic pump or a linear peristaltic pump. A peristaltic pump can convey the fluid through the delivery tubing 16 by way of intermittent forces placed on the external surface of the delivery tubing. Peristaltic pumps are often applied during use of the electrosurgical device 30 because the mechanical elements of the pump places forces on the external surface of the delivery tubing and do not come into direct contact with the fluid, which can reduce the likelihood of fluid contamination. Other examples of system 60 might not include a pump, and fluid can be is provided to the electrosurgical device 30 via gravity.

The example electrosurgical unit 10 is configured to provide both monopolar and bipolar RF power outputs to a specified electrosurgical instrument such as electrosurgical device 30 and a bipolar RF output to the charging circuit 35. In one example, the electrosurgical unit 10 can be used for delivery of RF energy to instruments indicated for cutting and coagulation of soft tissue and for delivery of RF energy concurrent with fluid to instruments indicated for hemostatic sealing and coagulation of tissue. In one example, the electrosurgical unit 10 is capable of simultaneously powering specified monopolar and bipolar electrosurgical instruments but may include a lock out feature preventing both monopolar and bipolar output from being simultaneously activated.

During monopolar operation of electrosurgical device 30, a first electrosurgical electrode, often referred to as an active electrode, is provided with electrosurgical device 30 while an indifferent, or neutral, electrode is provided in the form of a ground pad dispersive electrode located on a patient. For example, the ground pad dispersive electrode is typically on the back, buttocks, upper leg, or other suitable anatomical location during surgery. In such a configuration, the ground pad dispersive electrode is often referred to as a patient return electrode. An electrical circuit of RF energy is formed between the active electrode and the ground pad dispersive electrode through the patient.

During bipolar operation of electrosurgical device 30, a second electrode, often referred to as the return electrode providing a second electrical pole, is provided as part of the device 30. The ground pad dispersive electrode is not used. An electrical circuit of RF energy is created between the first and second poles of the device 30. The current no longer flows through the patient's body to the ground pad dispersive electrode, but rather through a localized portion of tissue between the poles of the device 30.

In one example, charging circuit 35 is configured to power an accessory providing a supplementary function. In one example, the accessory can be included on or coupled to the electrosurgical device 30. In another example, the accessory can be separate from the electrosurgical device. Still further, the accessory can be electrically coupled to but separate from the charging circuit 35. The accessory can include lamps, light emitting diodes, motors, heating elements, cooling elements, fluid control or other devices that use a continuous or intermittent DC current that may be independent of activation of the electrosurgical electrodes.

The electrosurgical device 30 in the example is connected to electrosurgical unit 10 via cables 24. Cable 24 includes plug 34 that connect with bipolar output receptacle 38 and plug 42 that connects with monopolar output receptacle on 46 the electrosurgical unit 10. In the example, electrosurgical unit 10 does not include a dedicated output to power the charging circuit 35 or an accessory to provide a supplementary function. Rather, plug 34, coupled to the bipolar receptacle 38, is also electrically coupled to the charging circuit 35 via conductor 68 in the example. In the case of an example monopolar electrosurgical device, the electrical device is electrically coupled to the monopolar output receptacle and the charging circuit is electrically coupled to the bipolar output receptacle. An example bipolar electrosurgical device and the charging circuit are electrically coupled to the bipolar output receptacle. In one example, a receptacle can correspond with an active electrode receptacle and one or more receptacles can correspond with controls on the electrosurgical device 30. Still further, a receptacle can correspond with a second active electrode receptacle. An additional cable may connect a ground pad electrode to a ground pad receptacle 56 of the electrosurgical unit 10. In some examples, delivery tubing 16 and cable 24 are combined to form a single cable 26.

The features of electrosurgical unit 10 described are for illustration, and the electrosurgical units suitable for use with device 30 may include some, all, or other features than those described below. In one example, the electrosurgical unit 10 is capable of operating in at least bipolar mode as well as a bipolar mode and a monopolar mode including multiple functions within the monopolar mode such as a monopolar cutting function, a monopolar coagulation function.

In the monopolar cutting function, monopolar RF energy is provided to the device 30 at a first power level and/or a first waveform (collectively first, or cutting RF energy setting). For example, cutting RF energy for a cut function may be provided at a relatively low voltage and a continuous current (100% on, or 100% duty cycle). Nominal impedance can range between 300 to 1000 ohms for the cutting function. At a power setting of 90 Watts for cutting, voltage can range from approximately 164 to 300 volts root mean square (RMS).

In the monopolar coagulation function, monopolar RF energy is provided to the electrode at a second power level and/or second waveform (collectively second, or coagulating RF energy setting) that is different than at least one of the first power level or the first waveform. For example, coagulating RF energy for a coagulation function may be provided at a relatively higher voltage than the cut voltage and with bursts of a pulsed current, such as 1% to 6% on and 99% to 94% off, respectively (or 1% to 6% duty cycle). Other duty cycles are contemplated.

The electrosurgical unit 10 may provide bipolar RF energy at a third power level and/or third waveform (collectively third, or hemostatic sealing RF energy setting) along with fluid for a (generally low voltage) hemostasis or tissue sealing function that may be the same as or different than the cutting and coagulating RF settings provided to the device 30 for the cut function or the coagulation function. In one example, hemostatic sealing energy can be provided with a continuous current (100% duty cycle). Nominal impedance can range between 100 to 400 ohms for the hemostatic sealing function. At a power setting of 90 Watts for hemostatic sealing, voltage can range from approximately 95 to 200 volts RMS.

In one example, the electrosurgical unit 10 provides RF energy to the active electrode as a signal having a frequency in the range of 100 KHz to 10 MHz. In some cases, this energy is applied in the form of bursts of pulses. In one example, each burst typically has a duration in the range of 10 microseconds to 1 millisecond. The individual pulses in each burst typically each have a duration of 0.1 to 10 microseconds with an interval between pulses of 0.1 to 10 microseconds. The actual pulses are often sinusoidal or square waves and bi-phasic, that is alternating positive and negative amplitudes. Several other features are described in U.S. Pat. No. 8,323,276, to Palanker et al., and incorporated by reference herein in its entirety to the extent it is not inconsistent with the present disclosure.

Still further, the electrosurgical unit 10 may provide bipolar energy at a fourth power level, frequency, and/or fourth waveform (collectively fourth or charging energy setting) to the charging circuit 35. The fourth energy setting may include relatively lower power level and frequency than the first, second, and third RF energy settings, such as a low voltage signal and a frequency that may be below RF range.

The electrical surgical unit 10 includes a power switch to turn the unit on and off and an RF power setting display to display the RF power supplied to the electrosurgical device 30. The power setting display can display the RF power setting numerically in a selected unit such as watts.

The example electrosurgical unit 10 includes an RF power selector comprising RF power setting switches that are used to select or adjust the RF power setting. A user can push one power setting switch to increase the RF power setting and push the other power setting switch to decrease the RF power setting. In one example, power setting switches are membrane switches, soft keys, or as part of a touchscreen. In another example, the electrosurgical unit may include more than one power selectors such as a power selector for monopolar power selection and a power selector for bipolar power selection. The electrosurgical unit can also include an RF power activation display having an indicator light that can illuminate when the RF power is activated either via a hand switch on the device 30, a foot switch, or other switch.

The example electrosurgical unit 10 can also include fluid flow rate setting display and flow rate setting selector. The display can include indicator lights, and the flow rate selector can include switches. Pushing one of the flow rate switches selects a fluid flow rate, which is than indicated in display.

While not being bound to a particular theory, the relationship between the variables of fluid flow rate Q (such as in units of cubic centimeters per minute (cc/min)) and RF power setting Ps (such as in units of watts) can be configured to inhibit undesired effects such as tissue desiccation, electrode sticking, smoke production, char formation, and other effects while not providing a fluid flow rate Q at a corresponding RF power setting Ps not so great as to disperse too much electricity and or overly cool the tissue at the electrode/tissue interface. Electrosurgical unit 10 is configured to increase the fluid flow rate Q generally linearly with an increasing RF power setting Ps for each of the three fluid flow rate settings of low, medium, and high.

Electrosurgical unit 10 can be configured to include control of the pump 22. In this example, the speed of the pump 22, and the fluid throughput, can be predetermined based on input variables such as the RF power setting and the fluid flow rate setting. In one example, the pump 22 can be integrated with the electrosurgical unit 10.

Several electrosurgical units, or generators, are described, for example, in U.S. patent application Ser. No. 14/927,999 to Smith, et al., titled RF Output Stage Switching Mechanism, filed Oct. 30, 2015; U.S. patent application Ser. No. 14/928,020 to Hubelbank, et al., titled Finger Switch Circuitry to Reduce Leakage Current, filed Oct. 30, 2015; U.S. patent application Ser. No. 14/927,969 to Smith, et al., titled Power Monitoring Circuitry and Method for Reducing Leakage Current in RF Generators, filed Oct. 30, 2015; and U.S. Patent Application Publication No. 2006/0149225 to McClurken, each assigned to the assignee of the present disclosure and incorporated by reference herein in their entireties to the extent they are not inconsistent with the present disclosure.

While electrosurgical device 30 and charging circuit 35 are described with reference to electrosurgical unit 10 and other elements of system 60, it should understood the description of the combination is for the purposes of illustrating system 60. It may be possible to use the electrosurgical device 30 and charging circuit 35 in other systems including a different electrosurgical units or the electrosurgical unit 10 may be used with other electrosurgical devices or charging circuits.

Figure 2:
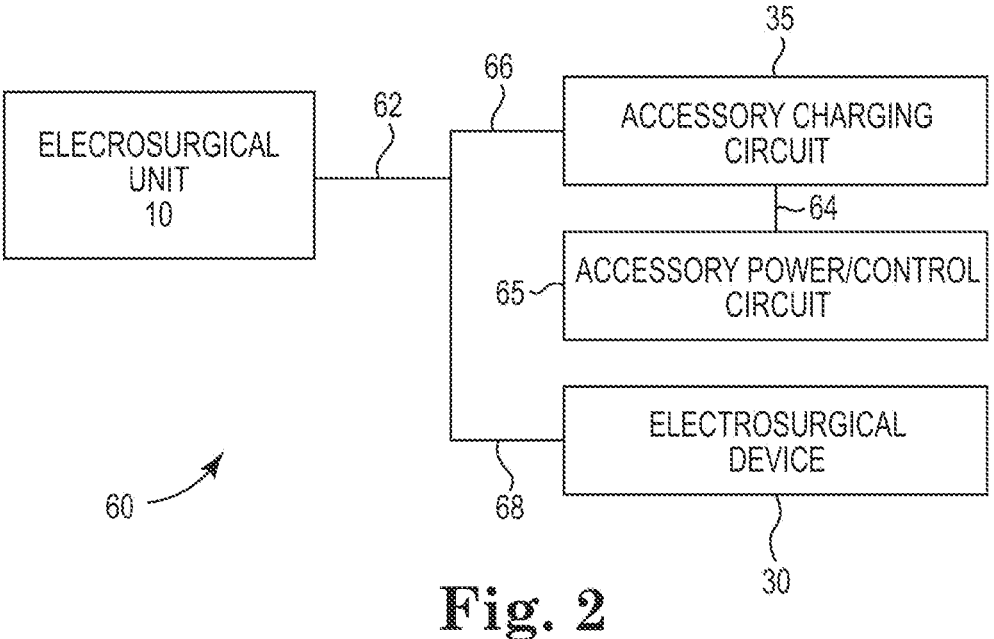
FIG. 2 is a block diagram illustrating an example of the electrosurgical system of FIG. 1 including the example electrosurgical unit, example accessory charging circuit, and example handheld electrosurgical device.

FIG. 2 illustrates an example implementation of the electrical couplings of electrosurgical system 60. Electrosurgical unit 10 is electrically coupled via conductors 62 to the electrosurgical device 30 and the accessory charging circuit 35. The accessory charging circuit 35 is electrically coupled to an accessory control/power circuit 65 via conductors 64. Conductors 62 includes conductors 66 electrically coupling the accessory charging circuit 65 to the electrosurgical unit 10 and at least conductor 68 electrically coupling the electrosurgical device 30 to the electrosurgical unit 10. In the case in which electrosurgical device 30 includes a bipolar mode, a plurality of conductors 68 are used to electrically couple the electrosurgical device 30 to the electrosurgical unit 10. In one example, the conductors 62 can be bundled together in a cable, such as cable 24. In another example, conductors 66, 68 can be included in separate cables.

In one example, conductors 66 are electrically coupled to the accessory charging circuit 35 and to the bipolar receptacle 38 of the electrosurgical device 10. The bipolar receptacle 38 includes a bipolar active connection and a bipolar return connection. In one example, one of conductors 66 is coupled to the bipolar active connection and another of conductors 66 is coupled to the bipolar return connection, such as via plugs.

The at least one conductor 68 is coupled to the monopolar output receptacle 46, the bipolar output receptacle 38, or both receptacles 38, 46. In an example of the electrosurgical device 30 including just a monopolar mode, conductor 68 is coupled to a monopolar active connection on the monopolar receptacle 46, such as via a plug. In an example of the electrosurgical device 30 including just a bipolar mode, conductors 68 can include at least two conductors, and one of conductors 68 is coupled to the bipolar active connection and another of conductors 68 is coupled to the bipolar return connection, such as via plugs. In the case of electrosurgical device 30 including both a monopolar mode and a bipolar mode, one of conductors 68 is coupled to a monopolar active connection on the monopolar receptacle 46, another of conductors 68 is coupled to the bipolar active connection and still another of conductors 68 is coupled to the bipolar return connection, such as via plugs.

In one example, the electrical electrosurgical device 30 and the accessory charging circuit 35 are coupled to a single cable, such as cable 24. In another example, the electrosurgical device 30 and the accessory charging circuit 35 are each coupled to separate cables, such as in an example in which the electrosurgical device is just operable in a monopolar mode.

Accessory control/power circuit 65 includes control and circuit elements to receive an electrical signal from accessory charging circuit 35 via conductors 64 to selectively power an accessory coupled to the control/power circuit 65. In one example, accessory control/power circuit 65 is selectively couplable to one or more accessories. For instance, the accessory control/power circuit 65 can include a receptacle that is couplable to the electrical connection on one or more accessories to provide power to the accessories. In another example, the accessory control/power circuit is integrally formed with an accessory. The control/power circuit 65 can include a binary controller, such an on/off switch, or a multivariate controller such as a plurality of settings such as a potentiometer or other adjustable control, to selectively provide a power or control setting to the accessory. For example, the control/power circuit can include an on/off switch to power a lamp, including a light emitting diode, or an adjustable control to select a brightness of illumination from one of several settings or from within a range of settings.

One or both of the accessory charging circuit 35 and the accessory control/power circuit 65 can be co-located with the surgical device 30. For example, the accessory control/power circuit 65 can be included within a housing of the surgical device 30 with conductors 64 connected to a remote accessory charging circuit 35 and conductors 68 connected to a remote electrosurgical unit 10. In another example, the accessory charging circuit 35 and the accessory control/power circuit 65 can be included within the housing of the surgical device. In these examples, an accessory may be included as part of the surgical device 30 or couplable to a receptacle connected to the surgical device 30. For instance, the accessory may be removably couplable to a receptacle located on the surgical device or on receptacle on a conductor attached to the surgical device 30. Thus, a clinician could selectively attach the accessory to the surgical device and operate the controls of the electrodes on the surgical device 30 as well as the control of the accessory on the surgical device.

The electrosurgical unit 10 can be configured to selectively provide an electrical signal of the charging energy setting to the accessory charging circuit 35 when connected via conductor 66. For example, a clinician may configure the electrosurgical unit 10 to provide the signal to the charging circuit 35, or the connected charging circuit 35 can cause the electrosurgical unit to automatically provide the signal via circuitry or other mechanism on the accessory charging circuit to alert the electrosurgical unit 10. The accessory charging circuit 35 can include a memory device to provide a selected signal to the electrosurgical unit 10 to automatically configure the electrosurgical unit 10 to the proper settings. Examples of a memory device can include a non-volatile memory device such as a read only memory (ROM), electronically programmable read only memory (EPROM), flash memory, non-volatile random access memory (NRAM) or other memory device. The accessory charging circuit 35 can also provide the selected signal to configure settings of the electrosurgical unit 10 with optical markings, radiofrequency identification (RFID) markers, or other mechanism to alert the electrosurgical unit 10 to automatically configure the settings to the charging energy setting.

The electrosurgical unit 10 can be configured to provide the charging energy setting to the charging circuit 35 when the electrosurgical device 30 is not activated and, in some instances, while the electrosurgical device is activated. In one example, the electrosurgical device can detect whether the electrosurgical device 30 is activated and, if activated, whether the electrosurgical device 30 is activated in a monopolar mode or a bipolar mode via internal circuitry, and provide an appropriate energy setting for output to the electrosurgical device 30. If the electrosurgical device 30 is not activated, the electrosurgical unit 10 can be configured to provide an appropriate energy setting to the charging circuit 30.

In some examples, no energy is provided to the accessory charging circuit when the electrosurgical device 30 is activated. A switch can be used to electrically isolate the electrosurgical unit 10 from the accessory charging circuit 35 or the electrosurgical unit 10 can provide no signal to the accessory charging circuit 35. The switch can be located on the electrosurgical device 30, activated as a footswitch or voice command operably coupled to the electrosurgical unit 10, or located on the electrosurgical unit 10.

In some examples, however, energy can still be provided to the accessory charging circuit 35 while the electrosurgical device 30 is activated. For example, if the electrosurgical device 30 is activated in monopolar mode and the electrosurgical unit 10 includes adequate signal isolation, the bipolar output of the electrosurgical unit 10 can continue to provide a bipolar signal to the accessory charging circuit 35. In some cases, the electrosurgical unit 10 can continue to provide a bipolar signal to the accessory charging circuit 35 while the electrosurgical device 30 is activated in bipolar mode.

Figure 3:
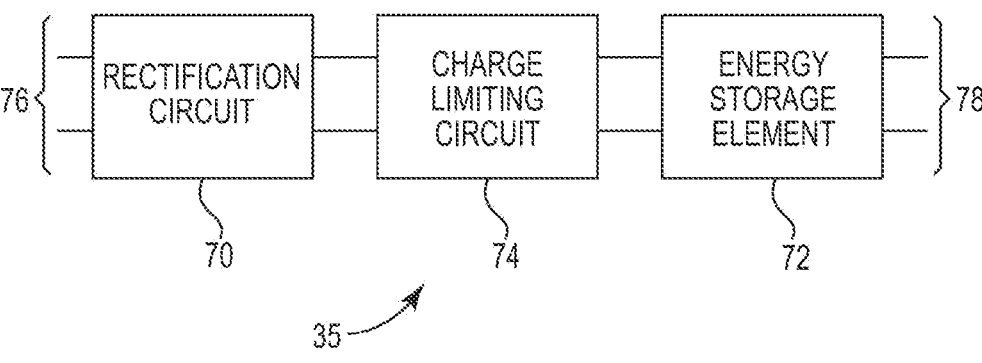
FIG. 3 is a block diagram illustrating an example accessory charging circuit of FIG. 1.

FIG. 3 illustrates an example accessory charging circuit 35. Example accessory charging circuit includes a rectification circuit 70 electrically coupled to the bipolar active connection and the bipolar return connection such as via conductors 66. The rectification circuit 70 is electrically coupled to an energy storage element 72. The energy storage element 72 includes connections to electrically couple with the accessory control/power circuit 65. The rectification circuit 70 receives bipolar RF energy from the bipolar receptacle of the electrosurgical unit, such as at the fourth, or charging RF energy setting, via electrical connections 76 couplable to conductors 66, and converts the alternating current of the RF energy signal into a direct current or rectified signal. The direct current is provided to the energy storage element 72, which can include a rechargeable battery, capacitor, or other element capable of storing electrical energy and selectively providing an energy output, via electrical connections 78 couplable to conductors 64, to the accessory control/power circuit 65. In one example, a charge limiting circuit 74 can be interposed between the rectification circuit 70 and the energy storage element 72 as indicated. The charge limiting circuit 74 is configured to prevent overcharging of the energy storage element 72 or to protect the energy storage element 72 from damage from receiving electrical energy after it has been fully charged.

Figure 4:
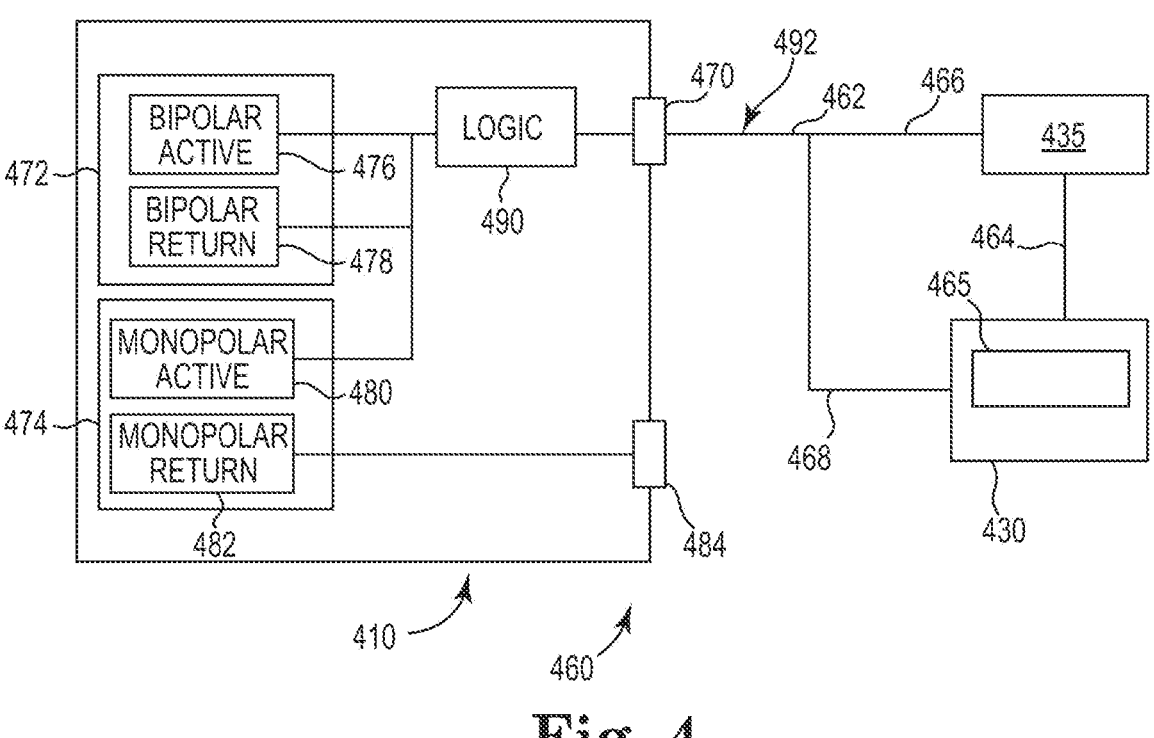
FIG. 4 is a block diagram illustrating a first example implementation of the example system of FIGS. 1 and 2.
Figure 5:
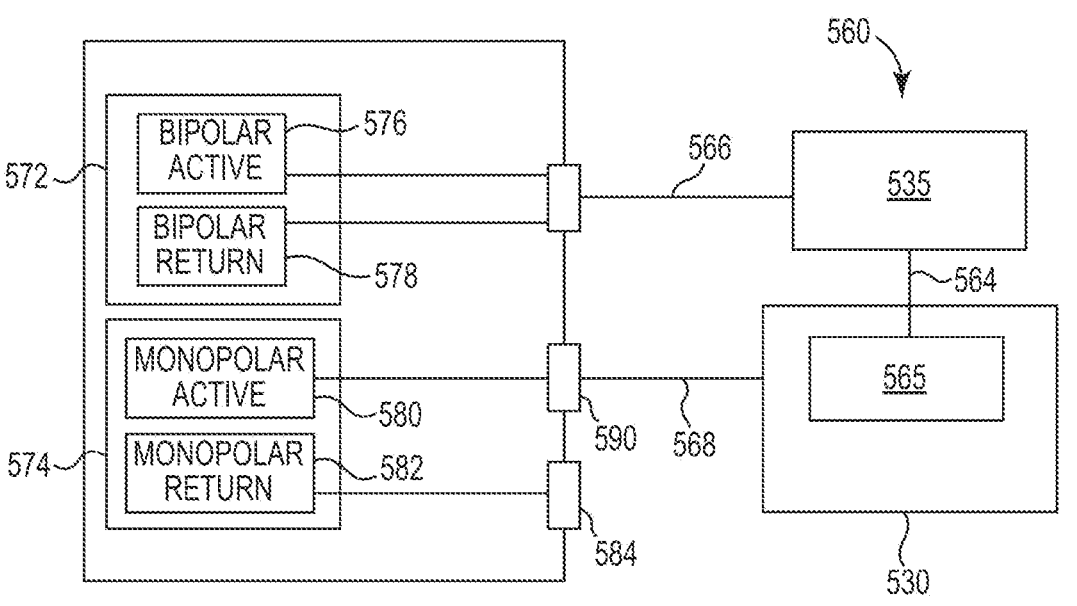
FIG. 5 is a block diagram illustrating a second example implementation of the example system of FIGS. 1 and 2.
Figure 6:
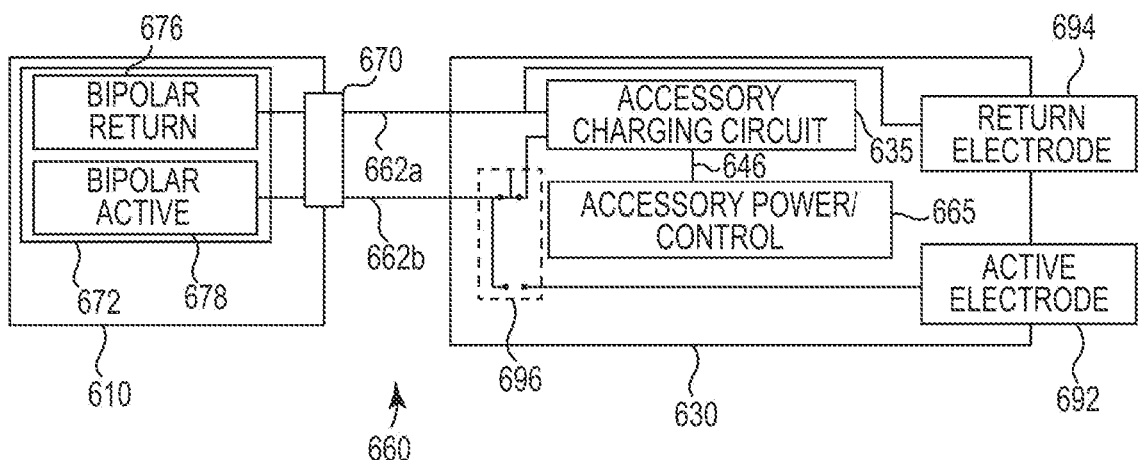
FIG. 6 is a block diagram illustrating a third example implementation of the example system of FIGS. 1 and 2.

FIGS. 4-6 illustrate examples of implementations of the system 60, and other example implementations are contemplate. FIG. 4 illustrates example system 460, which an implementation of system 60, having electrosurgical unit 410 operably coupled to electrosurgical device 430 and accessory charging circuit 435, corresponding with the features of electrosurgical unit 10, electrosurgical device 30, and accessory charging circuit 35, respectively. Example system 460 includes conductors 462 operably coupled to electrosurgical unit 410 as well as to electrosurgical device 430 and accessory charging circuit 435.

In one example, electrosurgical unit 410 includes an output connection 470 having capability to provide a monopolar RF energy signal and a bipolar RF energy signal. For example, the output connection 470 can correspond with a receptacle that accepts electrosurgical devices that can be operated in a monopolar mode or in a bipolar and monopolar mode. An example output connection of the output connection 470 a combination receptacle on an electrosurgical unit available under the trade designation AEX from Medtronic Advanced Energy, such as a seven-pin receptacle that accepts electrosurgical devices available under the trade designations PlasmaBlade and Combo from Medtronic Advanced Energy, LLC.

The electrosurgical unit 410 includes a bipolar circuitry 472 that can provide bipolar RF signals and monopolar circuitry 474 that are configured to provide monopolar RF signals. The bipolar circuitry 472 includes a bipolar active signal circuit 476 and a bipolar return signal circuit 478 that are provided to the output connection 470 via logic circuit 490. Additionally, the monopolar circuitry 474 includes a monopolar active signal circuit 480 that is provided to the output connection 470 via logic circuit 490. In the example, the monopolar circuitry 474 includes a monopolar return signal circuit 482 that is provided to a separate return pad connection 484 that can be operably coupled to a patient return electrode or pad (not shown).

Logic circuit 490 electrically couples the bipolar and monopolar circuitry 472, 474 to the output connection 470 and selectively provides electrical signals from the bipolar and monopolar circuitry 472, 474 to the output connection 470. The output connection 470 can be coupled to cabling or a cable 492 having conductors 462. Conductors 462 include conductors 466 that can be electrically coupled to the bipolar circuitry 472 and the accessory charging circuit 435 to provide a bipolar signal from bipolar circuitry 472 to the accessory charging circuit 435. Conductors 462 also include conductors 468 that can electrically couple the monopolar circuit 472, or monopolar active circuit 480, to the electrosurgical device 430 and provide a monopolar active signal from monopolar circuitry 474 to the electrosurgical device 430. In some examples, conductors 468 can electrically couple the bipolar circuitry 472 to the electrosurgical device 430 and also provide a bipolar signal from the bipolar circuitry 472 to the electrosurgical device 430.

Additionally, conductors 464 electrically couple the accessory charging circuit 435 to the accessory power/control circuit 465. In one example, the accessory charging circuit 435 includes an energy storage element such as a rechargeable battery, as set forth in FIG. 3, which is electrically coupled to the accessory power/control circuit 465 via conductors 464. The example illustrates accessory power/control circuit 465 included on electrosurgical device 430 and remote from accessory charging circuit 435, although alternative configurations are contemplated.

Figure 7:
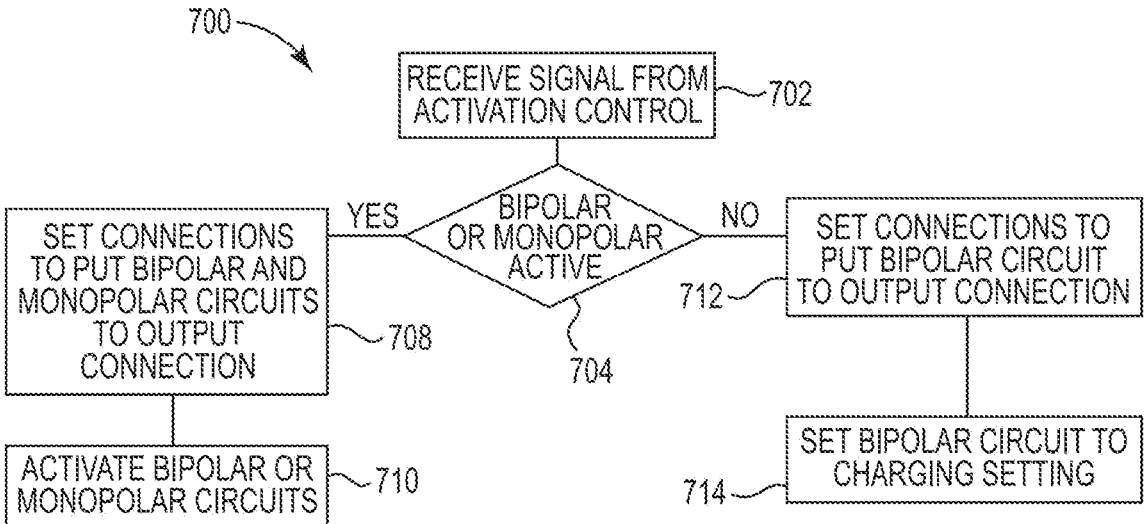
FIG. 7 is a flow diagram illustrating an example method of a logical process of a logic circuit of FIG. 4.

FIG. 7 illustrates an example method 700 of logic circuit 490. Logic circuit 490 is receives a signal form the activation control of the electrosurgical unit at 702. A determination is made at 704 as to whether a monopolar mode or bipolar mode have been activated, such as via the electrosurgical device 430, a footswitch, or other activation mechanism.

If the determination at 704 is that the monopolar mode or bipolar mode has been activated, switching circuitry, such as relays or other connection circuitry of the electrosurgical unit 410 are set to put the bipolar active and return circuits 476, 478 and the monopolar active circuit 480 in electrical connection with the output connection 470 at 708. The bipolar circuit 472 or monopolar circuit 474 are activated at 710 as selected by the electrosurgical device 430, or footswitch or other mechanism.

If the determination at 704 is that the monopolar mode and bipolar mode are not activated, switching circuitry, such as the relays or other connection circuitry of the electrosurgical unit 410 are set to output the bipolar circuit 472, such as the bipolar active and return circuitry 476, 478, in electrical connection with the output connection 470 at 712. The bipolar circuit 472 is set to provide the fourth, or charging energy setting at 714 to provide an electrical signal to the accessory charging circuit 435 via conductors 464.

Any combination of hardware and programming may be used to implement the functionalities of the example method 700. Such combinations of hardware and programming may be implemented in a number of different ways. For example, the programming for the electrosurgical unit 410, or 10, and method 700 may be processor executable instructions stored on at least one non-transitory machinereadable storage medium, and the hardware may include at least one processing resource to execute those instructions. In some examples, the hardware may also include other electronic circuitry to at least partially implement at least one feature of electrosurgical unit 410 and method 700. In some examples, the at least one machine-readable storage medium, such as a memory device, may store instructions that, when executed by the at least one processor, at least partially implement some or all features of electrosurgical unit 410 and method 700. In such examples, electrosurgical unit 410 may include the at least one machine-readable storage medium storing the instructions and the at least one processing resource to execute method 700. In other examples, the functionalities of electrosurgical unit 410 and method 700 may be at least partially implemented in the form of electronic circuitry. In one example, the hardware to implement the functionalities of the electrosurgical unit 410 are included in the electrosurgical unit available under the trade designation AEX from Medtronic Advanced Energy and the programming can be provided as a software upgrade or firmware upgrade to existing programming or firmware.

In an example implementation of the system 460 of FIG. 4, the electrosurgical unit 410 uses internal switching to route the bipolar signal to the output connector 470 when neither monopolar mode nor bipolar mode is activated and delivers low voltage energy to the accessory charging circuit 435. As set forth in the example of FIG. 3, this energy is rectified and stored in a capacitor, rechargeable battery or other similar energy storage element. When either monopolar mode or bipolar mode is activated, the electrosurgical unit 410 switches the outputs to an active state and delivers RF energy to the electrosurgical device 430 connected to the electrosurgical unit 410. With a shared active output connector 470 for both monopolar and bipolar modes, the output connector 470 may not be possible to deliver energy to the accessory charging circuit 435 using the bipolar output regardless of whether a bipolar electrosurgical device 430 is being used. Depending on isolation present in the electrosurgical unit 410 between the monopolar and bipolar circuits 472, 474, it may be possible to output energy to the accessory charging circuit 435 though the bipolar active and return circuits 476, 478 while using the electrosurgical device 430 in monopolar mode.

FIG. 5 illustrates example system 560, which an implementation of system 60, having electrosurgical unit 510 operably coupled to electrosurgical device 530 and accessory charging circuit 535, corresponding with the features of electrosurgical unit 10, electrosurgical device 30, and accessory charging circuit 35, respectively. Example system 560 includes conductor 568 operably coupled to a monopolar active output connection 590 on electrosurgical unit 510 as well as to electrosurgical device 530 and conductors 566 operably coupled to bipolar output connection 570 on the electrosurgical unit 510 and accessory charging circuit 535.

The electrosurgical unit 510 includes a bipolar circuitry 572 that can provide bipolar RF signals and monopolar circuitry 574 that are configured to provide monopolar RF signals. The bipolar circuitry 572 includes a bipolar active signal circuit 576 and a bipolar return signal circuit 578 that are provided to the bipolar output connection 570. Additionally, the monopolar circuitry 574 includes a monopolar active signal circuit 580 that is provided to the monopolar active output connection 490. In the example, the monopolar circuitry 574 includes a monopolar return signal circuit 582 that is provided to a separate return pad connection 584 that can be operably coupled to a patient return electrode or pad (not shown).

Additionally, conductors 564 electrically couple the accessory charging circuit 535 to the accessory power/control circuit 565. In one example, the accessory charging circuit 535 includes an energy storage element such as a rechargeable battery, as set forth in FIG. 3, which is electrically coupled to the accessory power/control circuit 565 via conductors 564. The example illustrates accessory power/control circuit 565 included on electrosurgical device 530 and remote from accessory charging circuit 535, although alternative configurations are contemplated.

System 560 incorporates dual connectors 570, 590, one connected to the monopolar output and one connected to the bipolar output. System 560 provides for the monopolar circuitry 574 to activate electrosurgical device 530. The bipolar circuitry 572 can continuously provide an fourth energy signal to the accessory charging circuit 535, and thus could be applied to accessories that draw relatively large amounts of power. System 560 may also be applied for a system that does not route bipolar RF energy to the same connector as the monopolar output in a combination connector such as the connector 470 of FIG. 4.

FIG. 6 illustrates example system 660, which an implementation of system 60, having electrosurgical unit 610 operably coupled to electrosurgical device 630 and accessory charging circuit 635, corresponding with the features of electrosurgical unit 10, electrosurgical device 30, and accessory charging circuit 35, respectively.

Electrosurgical unit 610 includes bipolar circuitry 672 to provide a bipolar RF signals to electrosurgical device 630 as well as a low power signal to accessory charging circuit 635. The bipolar circuitry 672 includes a bipolar active signal circuit 676 and a bipolar return signal circuit 678 that are provided to a bipolar output connection 670 via logic circuitry (not show) that can activate either the bipolar RF signal or the low power signal to the accessory charging circuit 635.

Electrosurgical device 630 includes a bipolar active electrode 692, bipolar return electrode 694, and selector switch 696 to activate the bipolar mode. In the example, the accessory charging circuit 635 is co-located with the electrodes 692, 694 on the electrosurgical device, although other examples are contemplated. An accessory power/control circuit 665 is also included on the electrosurgical device 630, but other configurations of the accessory charging circuit 635 and accessory power/control circuit 665 are contemplated.

In the example, the bipolar return signal circuit 678 is electrically coupled to the bipolar return electrode 694 and the accessory charging circuit 635 via conductor 662a. The bipolar active signal circuit 676 is electrically coupled to the accessory charging circuit 635 via selector switch 696. The selector switch 696 can be used to electrically couple the bipolar active signal circuit 676 to the bipolar active electrode 692 via conductor 662b.

The example system 660 provides an output via the bipolar circuitry 672 to the accessory charging circuit 635 when the bipolar mode in not activated is off. The bipolar signal from the bipolar circuitry 672 can be switched between the electrodes 692, 694 and the accessory charging circuit 672 either through the use of a multicontact pushbutton as selector switch 696 in the electrosurgical device 630 or through switching circuitry such as relay controlled by the electrosurgical unit 610 and activated by a footswitch or other switching mechanism.

Although the present disclosure has been described with reference to preferred embodiments, workers skilled in the art will recognize that changes can be made in form and detail without departing from the spirit and scope of the present disclosure.

What is claimed is:

1. A method for operating an electrosurgical system including an electrosurgical device operable in at least one of a monopolar mode and a bipolar mode, the method comprising:

determining whether a bipolar mode or monopolar mode of the electrosurgical device has been activated, wherein the electrosurgical device is operable in the monopolar mode via a received monopolar RF energy signal of at least one of a first power waveform and a second power waveform, and wherein the electrosurgical device is operable in the bipolar mode via a received bipolar RF energy signal of a third power waveform, wherein the first power waveform, the second power waveform and the third power waveform each provide different power levels and frequency ranges;

operably coupling a monopolar active circuit and bipolar active and return circuits in electrical connection with an output connection and activating one of monopolar circuitry and bipolar circuitry based on which of the monopolar mode and the bipolar mode of the electro-surgical device has been activated;

operably coupling the bipolar active circuit in electrical connection with the output connection and activating the bipolar circuitry if the electrosurgical device is not activated; and operably coupling an accessory charging circuit to an accessory, the accessory charging circuit configured to receive a bipolar signal of a fourth power waveform, the fourth power waveform below an RF range relative to the first, second, and third power waveforms.

2. The method of claim 1, wherein the bipolar circuitry provides a bipolar RF energy signal if the bipolar mode is activated and a bipolar energy signal if the bipolar mode is not activated.

3. The method of claim 2, wherein the bipolar energy signal includes a lower voltage than the bipolar RF energy signal.

4. The method of claim 3, wherein the bipolar energy signal includes a lower frequency than the bipolar RF energy signal.

5. The method of claim 1, wherein the accessory charging circuit is configured to receive the bipolar signal of the fourth power waveform when the monopolar mode is acti-vated.

6. A method for operating an electrosurgical system including an electrosurgical device operable in at least one of a monopolar mode and a bipolar mode, the method comprising:

determining whether a bipolar mode or monopolar mode of the electrosurgical device has been activated, wherein the electrosurgical device is operable in the monopolar mode via a received monopolar RF energy signal of at least one of a first power waveform and a second power waveform, and wherein the electrosur-gical device is operable in the bipolar mode via a received bipolar RF energy signal of a third power waveform, wherein the first power waveform, the sec-ond power waveform and the third power waveform each provide different power levels and frequency ranges;

operably coupling a monopolar active circuit and bipolar active and return circuits in electrical connection with an output connection and activating one of monopolar circuitry and bipolar circuitry based on which of the monopolar mode and the bipolar mode of the electro-surgical device has been activated;

operably coupling the bipolar active circuit in electrical connection with the output connection and activating the bipolar circuitry if the electrosurgical device is not activated, wherein the bipolar circuitry is configured to provide a bipolar energy signal when the monopolar mode is activated; and operably coupling an accessory charging circuit to an accessory, the accessory charging circuit configured to provide power to the accessory, wherein the accessory charging circuit is configured to receive a bipolar signal of a fourth power waveform, the fourth power waveform below an RF range relative to the first, second, and third power waveforms.

7. The method of claim 6, wherein the bipolar circuitry provides a bipolar RF energy signal if the bipolar mode is activated and a bipolar energy signal if the bipolar mode is not activated.

8. The method of claim 7, wherein the bipolar energy signal includes a lower voltage than the bipolar RF energy signal.

9. The method of claim 7, wherein the bipolar energy signal includes a lower frequency than the bipolar RF energy signal.

10. A method for operating an electrosurgical system including an electrosurgical device operable in at least one of a monopolar mode and a bipolar mode, the method comprising:

determining whether a bipolar mode or monopolar mode of the electrosurgical device has been activated, wherein the electrosurgical device is operable in the monopolar mode via a received monopolar RF energy signal of at least one of a first power waveform and a second power waveform, and wherein the electrosur-gical device is operable in the bipolar mode via a received bipolar RF energy signal of a third power waveform, wherein the first power waveform, the sec-ond power waveform and the third power waveform each provide different power levels and frequency ranges;

operably coupling a monopolar active circuit and bipolar active and return circuits in electrical connection with an output connection and activating one of monopolar circuitry and bipolar circuitry based on which of the monopolar mode and the bipolar mode of the electro-surgical device has been activated;

operably coupling the bipolar active circuit in electrical connection with the output connection and activating the bipolar circuitry if the electrosurgical device is not activated, wherein the bipolar circuitry is configured to provide a bipolar energy signal when the monopolar mode is activated; and operably coupling an accessory charging circuit to an accessory, the accessory charging circuit configured to provide power to the accessory, wherein the bipolar circuitry is configured to provide bipolar energy to the accessory charging circuit when the monopolar mode is activated.

11. The method of claim 10, wherein the bipolar circuitry provides a bipolar RF energy signal if the bipolar mode is activated and a bipolar energy signal if the bipolar mode is not activated.

12. The method of claim 11, wherein the bipolar energy signal includes a lower voltage than the bipolar RF energy signal.

13. The method of claim 11, wherein the bipolar energy signal includes a lower frequency than the bipolar RF energy signal.

* * * * *